United States Patent
Stanford et al.

(10) Patent No.: US 9,784,563 B2
(45) Date of Patent: Oct. 10, 2017

(54) CALIBRATING THE POSITIONS OF A ROTATING AND TRANSLATING TWO-DIMENSIONAL SCANNER

(75) Inventors: Alan R. Stanford, Eaton, OH (US); David C. Woo, Foster City, CA (US); John David Morgenthaler, Menlo Park, CA (US)

(73) Assignee: Applied Biosystems, LLC, Carlsbad, CA (US)

(*) Notice: Subject to any disclaimer, the term of this patent is extended or adjusted under 35 U.S.C. 154(b) by 0 days.

(21) Appl. No.: 12/875,995

(22) Filed: Sep. 3, 2010

(65) Prior Publication Data

US 2011/0137600 A1  Jun. 9, 2011

Related U.S. Application Data

(63) Continuation of application No. 12/021,000, filed on Jan. 28, 2008, now abandoned.

(60) Provisional application No. 60/898,281, filed on Jan. 30, 2007.

(51) Int. Cl.
| | |
|---|---|
| *G01C 17/38* | (2006.01) |
| *G01B 11/00* | (2006.01) |
| *G01B 11/26* | (2006.01) |
| *B01L 9/00* | (2006.01) |
| *G01N 35/00* | (2006.01) |

(52) U.S. Cl.
CPC ............ *G01B 11/002* (2013.01); *G01B 11/26* (2013.01); *B01L 9/523* (2013.01); *G01N 35/00584* (2013.01)

(58) Field of Classification Search
CPC .............................. G01B 11/002; G01B 11/26
USPC .............................................. 702/94; 73/1.81
See application file for complete search history.

(56) References Cited

U.S. PATENT DOCUMENTS

| | | | | |
|---|---|---|---|---|
| 4,344,142 A | * | 8/1982 | Diehr, II | B29C 35/0288 264/325 |
| 2003/0143751 A1 | * | 7/2003 | Corson | G01N 21/253 436/164 |
| 2004/0022677 A1 | * | 2/2004 | Wohlstadter | B01L 3/5085 422/52 |
| 2004/0224332 A1 | * | 11/2004 | Loney | G06K 9/00127 435/6.19 |
| 2007/0035818 A1 | * | 2/2007 | Bahatt | G01N 21/253 359/366 |
| 2008/0012850 A1 | * | 1/2008 | Keating, III | H04N 13/0207 345/419 |

OTHER PUBLICATIONS

Supreme Court Decision (*Alice* vs *CLS Bank*) (2013).*

* cited by examiner

*Primary Examiner* — Hyun Park

(57) ABSTRACT

Systems and methods are provided that comprise calibration techniques and associated systems that identify the two-dimensional position, or other alignment or positioning, of sample wells or other calibration objects located in a sample well plate, or other surface or area of interest. In some embodiments, calibration of the plate and/or positioning and/or alignment with respect to detection optics can be performed in multiple stages for two or more dimensions.

15 Claims, 8 Drawing Sheets

CALIBRATING THE POSITIONS OF A ROTATING AND TRANSLATING TWO-DIMENSIONAL SCANNER

RELATED APPLICATION

This application in a continuation of U.S. patent application Ser. No. 12/021,000 filed Jan. 28, 2008, which claims priority to U.S. Provisional Application No. 60/898,281 filed Jan. 30, 2007, entitled "Calibrating the Positions of a Rotating and Translating Two-Dimensional Scanner," all of which are incorporated herein in its entirety by reference.

BACKGROUND

Polymerase chain reaction (PCR) and other detection systems rely upon the accurate and consistent positioning of sample well plates, and other carriers or supports, to perform accurate measurements of sample fluorescence in arrays of sample wells. When the 96 or other number of sample wells in a standard microtitre plate, or other plate configuration, are not accurately aligned with the read path of the optical detector, the peak signal intensities associated with individual wells can be incorrectly measured and recorded. Systems employing spectral filters on the detection optics can likewise experience spectral shifts when the filter optics are skewed from desired alignments. Other detection artifacts can occur when the detection or imaging optics are not accurately aligned with the sample wells, or other detection regions. Correct detection and alignment of the optical reader with the sample wells is a significant objective for these and other detection systems.

SUMMARY

According to various embodiments of the present teachings, systems and methods are provided which scan or image the sample wells of a sample plate, or other calibration objects or features, and capture the fluorescent dye or other emission amplitudes and spectra to generate an accurate positional calibration or alignment setting of the plate and wells or other calibration objects. In some embodiments, the sample wells can be loaded with reference fluorescent dyes, and, for example, scanned using a photodiode or other detection device, to record intensity peaks and locations. The photodiode or other detection devices can be mounted in a rotating scan head which can move across the plate in an arc pattern to locate over individual columns in a sample well grid. The scan head can also move in a translational direction, for example, up and down along columns or lines, to detect the successive rows, or other sample supports, or other features of well emissions.

According to various embodiments, the raw scanned or imaged data can contain positional or geometric distortions, because the scan head moves along an arc-shaped rotational sweep as it moves in its angular degree of freedom. In some embodiments, the calibration analysis can locate peak pixels of individual wells, and determine the average or mean separation of the wells in an effort to calibrate, shift, or realign the well peaks to produce a non-distorted representation of the sample plate, and the wells in the sample plate. Subsequent scans of the samples wells conducted, for example, during PCR or other operational runs, can make use of the calibrated plate alignment to simplify optical scans by taking intensity readings along only the calibrated column and row coordinates. The speed and accuracy of data collection can be increased, among other advantages.

FIGURES

Figure 7A:
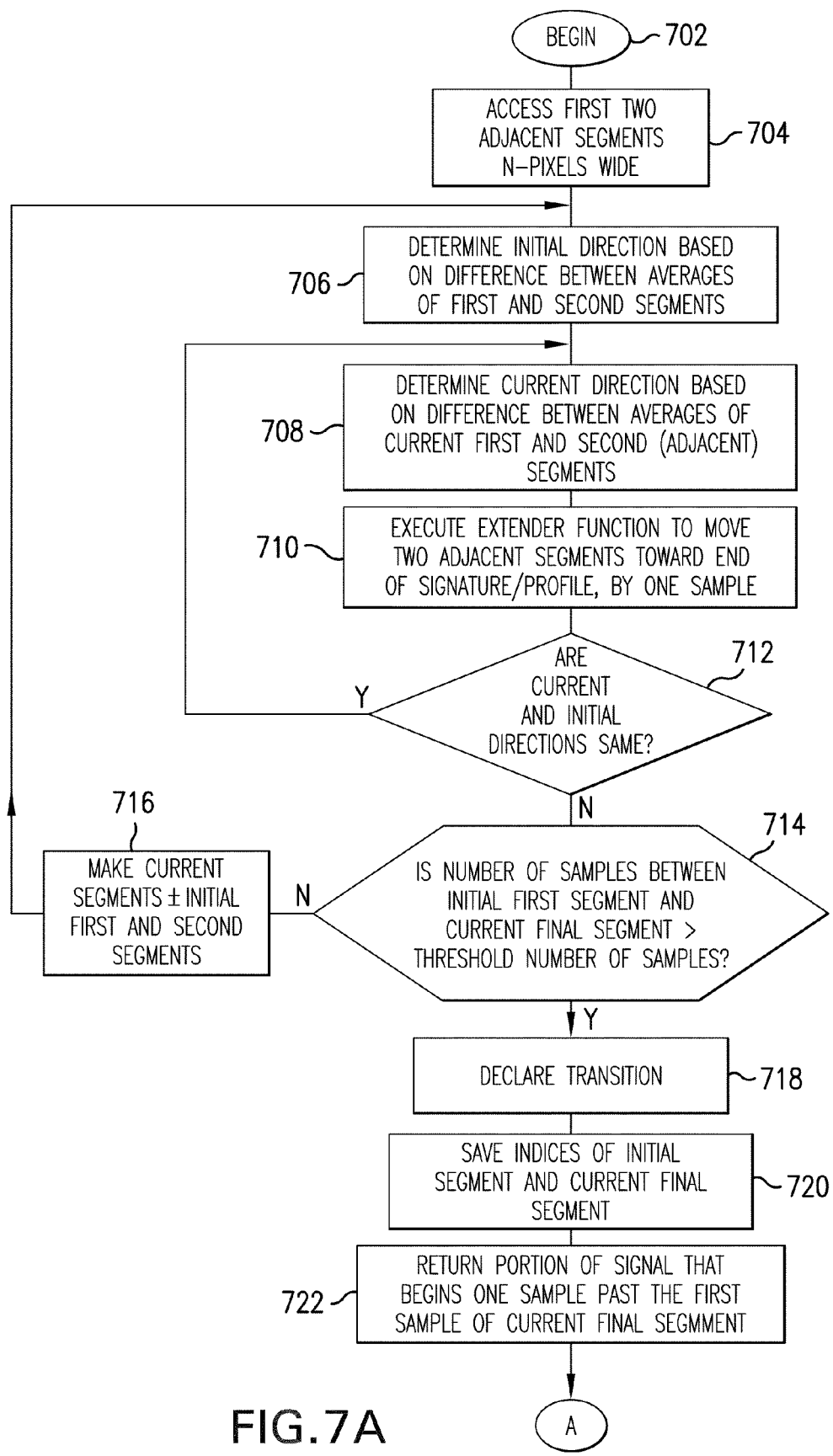
Figure 7B:
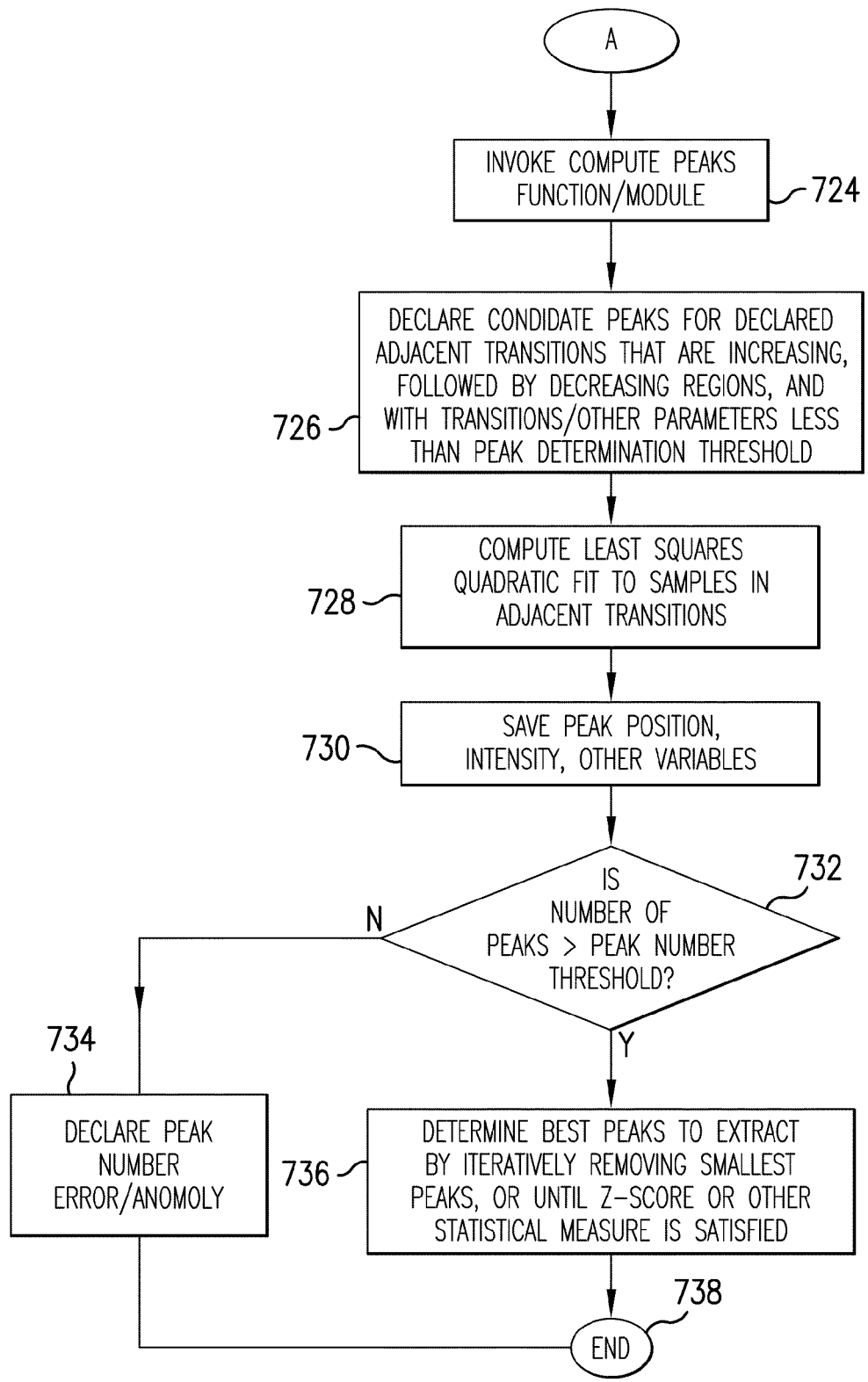

FIGS. 7(A) and 7(B) illustrate a flowchart of peak detection and processing, according to various embodiments of the present teachings.

DESCRIPTION

According to various embodiments of the present teachings, calibration of the output signal location readings of a sample well plate, can be performed to maximize the accuracy and consistency of spectral and/or other readings. In some embodiments, the calibration can be conducted using a sample well plate and an associated optical reader which can be or can comprise a real-time polymerase chain reaction (PCR), or other system. According to various embodiments, the calibration systems and methods can be implemented in or applied to PCR scanning systems in which a read head containing a photodetector, for example, a photodiode or other detector, can read the fluorescent output or other output from a single well or location at a time, then travel to a next well or location to read the spectral dye or other output at that location, and step or repeat across a plate or other container or platform to take spectra from the entire group of sample wells. The calibration systems and methods can be implemented in or applied to PCR imaging system, in which a photodetector, for example, a CCD, CID or other detector, images an entire plate and all sample wells contained therein at one time or substantially one time, for instance, taking a spectral image of all 96 or other number of wells of a standard microtitre plate. According to various embodiments, each well or other container or location in a plate or other platform can contain samples, for example, samples of DNA fragments or other material, to which one or more spectrally distinct dyes can be attached for detection and analysis.

Herein, the term "emission" is used to exemplify a signal detected and/or calibrated according to various embodiments of the present teachings. It is to be understood that by "emission" the present teachings are referring to not only electromagnetic radiation but rather are also referring to any physical or chemical signal or other data that can be read, detected, imaged, or surmised from one or more area of interest, for example, a support region such as a well of a multi-well plate. "Emission" herein is intended to encompass electromagnetic radiation, optical signals, chemiluminescent signals, fluorescent signals, radiation transmission values, and radiation absorption values.

Figure 1:
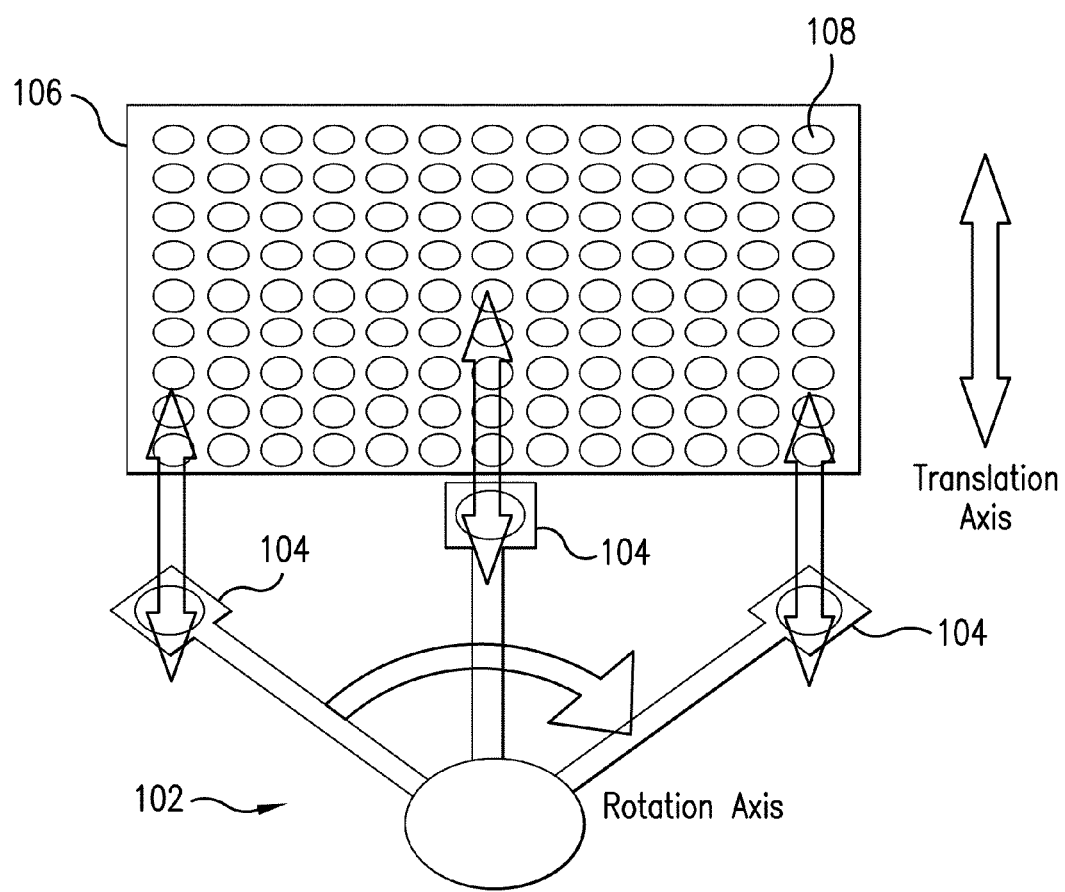
FIG. 1 illustrates rotating and translating a two-dimensional scanner, according to various embodiments of the present teachings.

According to various embodiments, for example, as generally depicted in FIG. 1, the calibration can comprise rotating and translating a two-dimensional scanner 102 that moves a set of imagers 104 across an area of interest on a sample well plate 106 or other surface or support. According to various embodiments, each of the set of imagers 104 can comprise a single-pixel imager element, for example, a photodiode. Each of the set of imagers 104 can comprise a multiple-pixel imager element, for example, a charge coupled device (CCD). According to various embodiments, other imaging elements and arrangements of those elements can be used, for example, a photomultiplier tube. According to various embodiments, each set of imagers 104 can comprise, as shown, a set of three imagers, and each can be equipped with a distinct spectral filter, to filter and image emission of different wavelengths resulting from the imaged samples. Different amounts of filters can be used.

According to various embodiments, the area of interest on sample well plate 106 can contain, for example, a precision rectangular grid of calibration objects, such as the regularly spaced sample wells 108 of sample plate 106, as shown. The wells 108 or other calibration objects can be used, for example, for PCR or other amplification or other reactions. As shown, instrument fixtures such as a mounting block, heater block, or other structure or support in which plate 106 can be mounted or registered, can align one axis of the rectangular grid of wells 108 or other calibration objects with the translational motion of scanner 102.

According to various embodiments, the scanner 102 can be calibrated, for example, to accurately move to positions centered on the wells 108 or other calibration objects in the rectangular grid of plate 106, or other surface or sample support. The calibration analysis can comprise inspecting at least two images taken of plate 106 and/or wells 108, and computing the rotational and translational positions of the array of wells 108, which correspond to positions in the rectangular grid of plate 106 or locations in another array or pattern.

Figure 2:
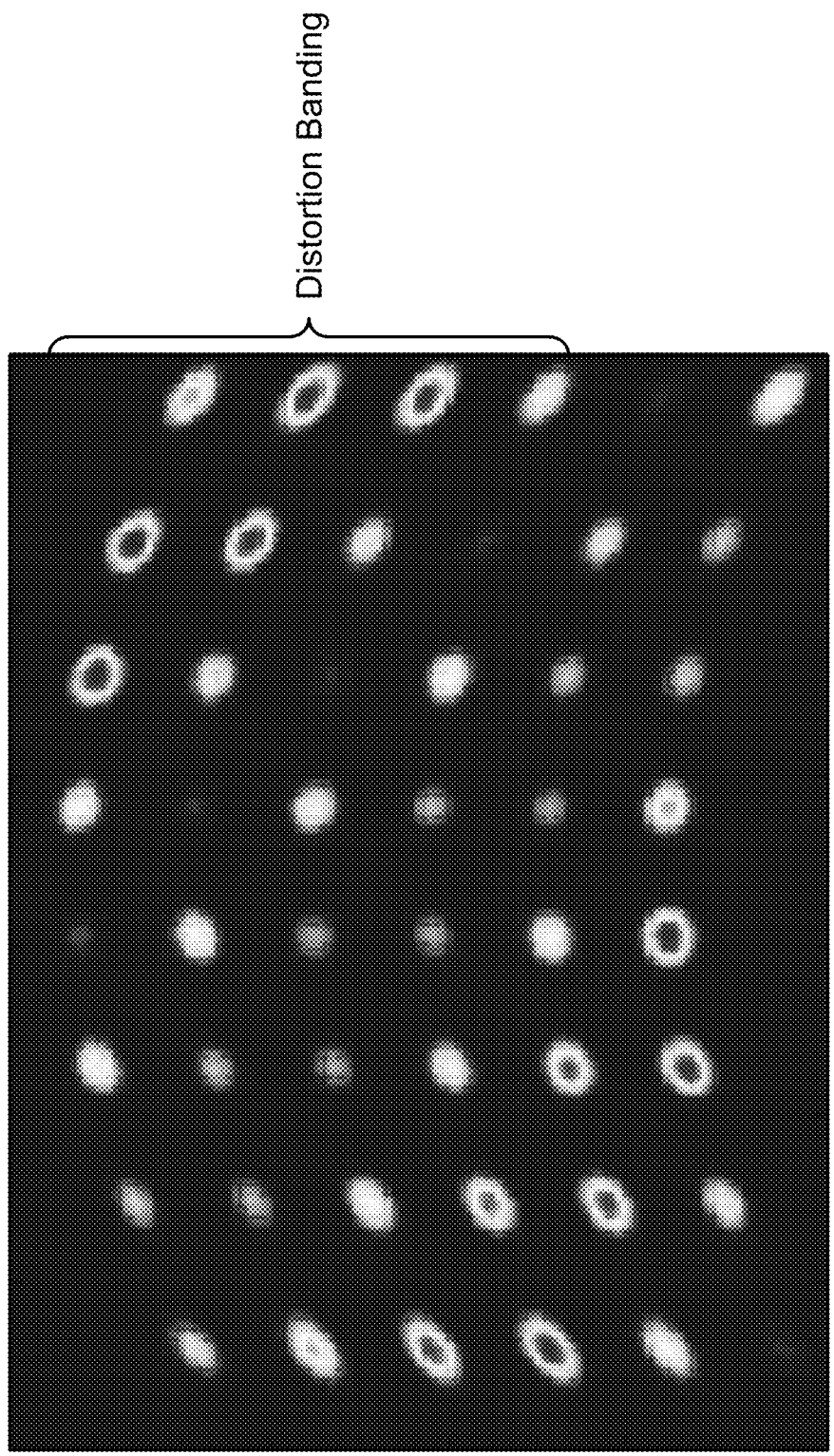
FIG. 2 illustrates a rotation calibration image including a distorted image of a rectangular grid of objects, according to various embodiments of the present teachings.

According to various embodiments, the calibration analysis can comprise acquiring every column of the at least two images inspected by rotating the head of the scanner 102 to an angular or rotational position (labeled θ, theta), by holding that rotational position, by translating to a start position, by acquiring image pixels of plate 106 or other objects, by translating to a stop position, and by finishing the acquisition of image pixels of plate 106 or other objects. The motion of the scan head of scanner 102 can be step-wise, for example, using a stepper motor to rotate or translate the head of scanner 102. The motion of the scan head of scanner 102 can be continuous, without intermittent start and stop actions. According to various embodiments, all columns of the rotational calibration image taken of plate 106 can begin and stop at the same translational or linear position, but can have different rotational and/or angular positions. The rotational or angular position can be represented by angle θ (theta), or other parameter. According to various embodiments, the rotational (θ) measurement positions across plate 106 can be uniformly spaced, for example, as the head of the scanner 102 traces an arc which lines up with columns of plate 106. As the set of imagers 104 moves across plate 106 and takes images of emissions from wells 108 or other calibration objects, a distorted image of the rectangular grid of objects from each filter can result, for example, as illustrated in FIG. 2.

According to various embodiments, the column coordinate can be defined as the rotational position (θ) at which a pixel is acquired. In some embodiments, the row coordinate can be defined as the translational position at which a pixel was acquired. According to various embodiments, the column coordinates of the objects in the same row of rectangular grid of wells 108 (e.g., the first object in the columns) can form an arc or curve in the raw image.

Figure 3:
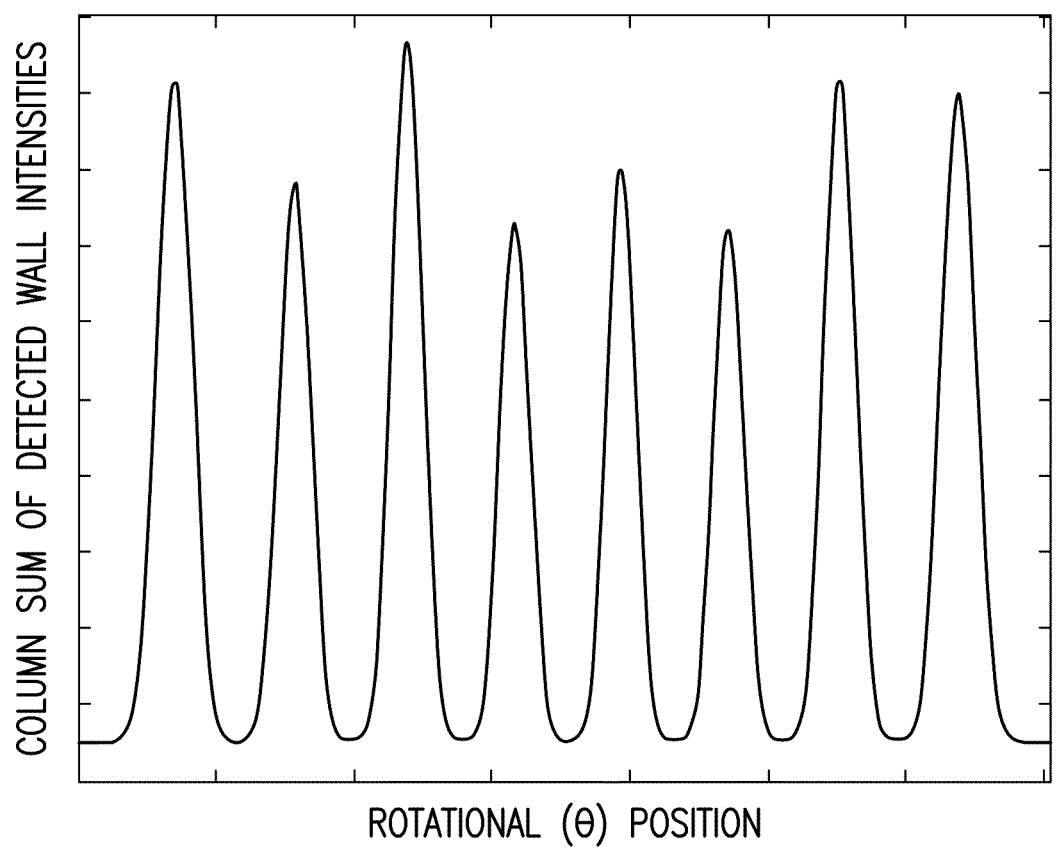
FIG. 3 illustrates a graph of image intensities summed along the direction of translation, according to various embodiments of the present teachings.

According to various embodiments, the calibration can comprise a first calibration or processing stage, to determine the rotational (θ) positions of the centers of the wells 108, or other calibration objects. The calibration analysis can comprise summing the image intensities for emissions from each well 108, detected in each column of plate 106, at a single rotational (θ) position along the direction of linear translation of scanner 102. A typical result of this summation is illustrated, for example, in FIG. 3. In various embodiments as shown, the positions of the detected signal peaks correspond to the rotational centers of the wells 108, because the brightest of most intensity signal amplitudes combine down the centerline of a column of wells 108. This analysis, in one regard, can more accurately anchor or locate the angular or rotational (θ) positions of well columns in plate 106. Differencing the image intensities for emissions from each well 108, detected in each column of plate 106, at a single rotational (θ) position along the direction of linear translation of scanner 102, can instead or additionally be used to determine the rotational centers of the wells.

Figure 4:
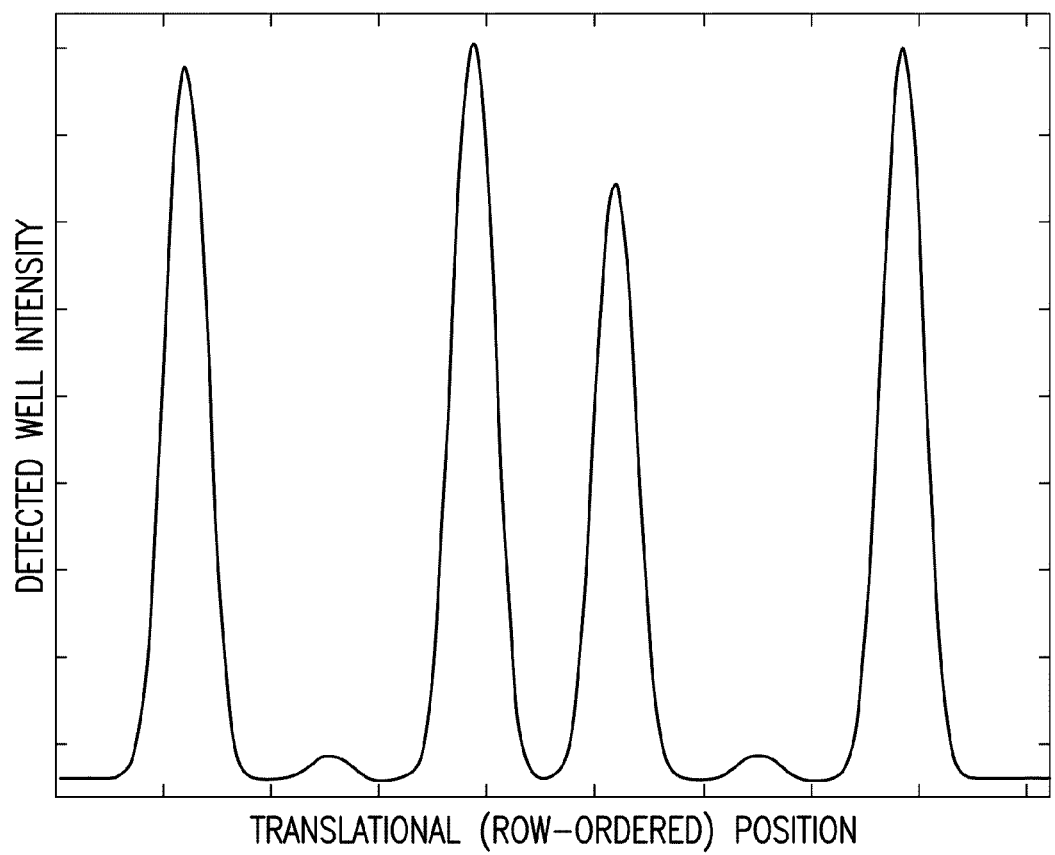
FIG. 4 illustrates a graph of image intensities of a single column of a rotation calibration image, according to various embodiments of the present teachings.

According to various embodiments, the calibration analysis can comprise a second calibration or processing stage, which can compute the column-dependant translational coordinates, which in contrast to rotational coordinates, will produce an undistorted image. The calibration analysis can find or detect the row positions (translational coordinates) of wells 108, or other calibration objects. These positions correspond to peak locations of wells 108 in single columns of the rotational calibration image. Conversely, the column positions correspond to rotational centers of columns of wells 108. FIG. 4, for example, shows one such single column of the rotational calibration image, including a set of peaks associated with emissions from successive rows which can be encountered in a column, according to various embodiments.

According to various embodiments, the calibration analysis can comprise a third calibration or processing stage, which can inspect a new or further image, the "translation calibration image," to determine or adjust the translational positions of the calibration objects. An exemplary translation calibration image is illustrated, for example, in FIG. 5.

According to various embodiments, the results of the first and second steps or stages can create a list of initial and final translational positions. In some embodiments, one list can be created for each column (rotational position) of the sample wells 108, or other calibration objects. The initial and final positions can be offset from, or correspond to, the first and last wells 108 by a distance equal to the average within-column (translational) separation of all the wells 108, or other calibration objects.

Figure 6:
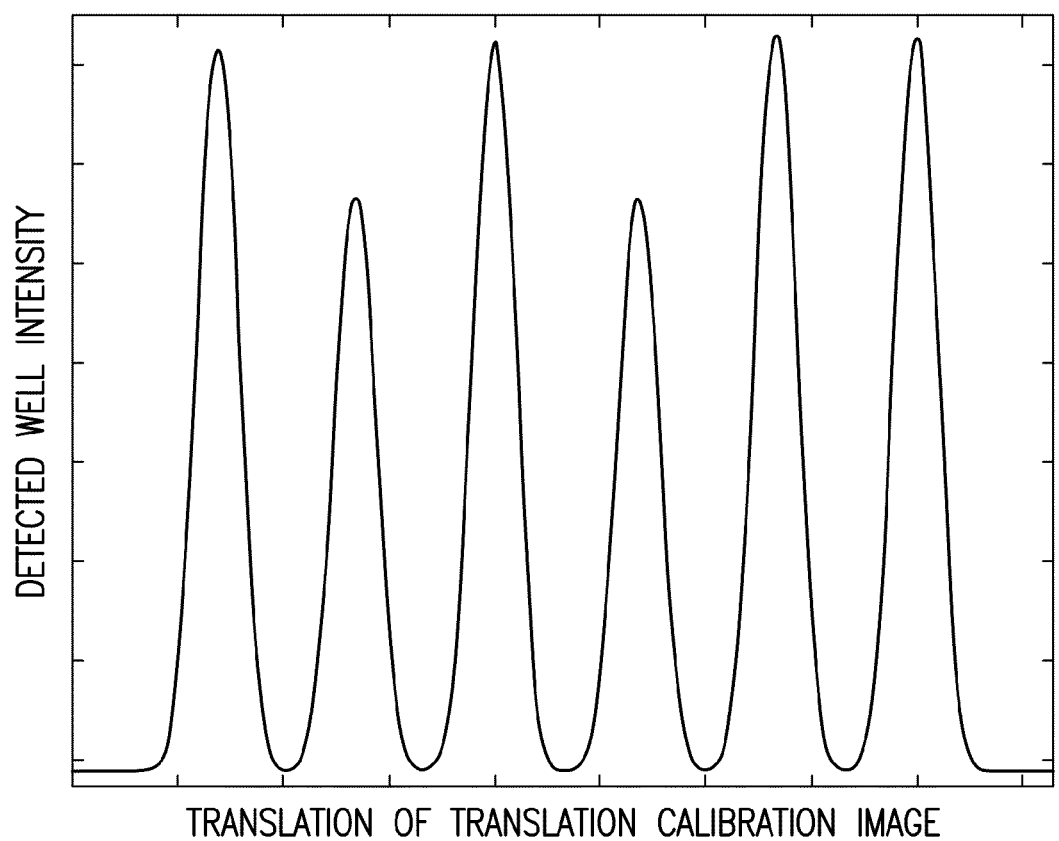
FIG. 6 illustrates a graph of image intensities across the direction of rotation, according to various embodiments of the present teachings.

According to various embodiments, the calibration analysis can comprise generating or manipulating a translation calibration image containing an equal amount of columns as there are columns of wells 108, or other calibration objects in original plate 106, with offsets to remove the arcing present in the original raw plate image. Each image column is centered on a different column of wells 108 or other calibration objects. The peak intensities in each column of the translation calibration image can correspond to the translational centers of the wells 108 or other calibration objects. FIG. 6, for example, illustrates one column of the translation calibration image, after translational offset or adjustment.

According to various embodiments, once the column positions have been accurately determined, processing of PCR or other runs can be performed using one image line, which can proceed down the determined center of each well for each column, with sample peaks determined from that single position. Actual processing runs can use the same or different optical resolution settings as the positional calibration processing. According to various embodiments, the PCR or other processing runs can, for instance, use a lower resolution to capture raw peak data, in part because there is increased confidence regarding data accuracy once positional calibration has been performed. One peak or amplitude can be captured for each well or other sample support or area of interest. In some embodiments, multiple intensity data points can be captured for each well.

According to various embodiments, each of rotational (column-oriented) and row alignment calibrations can be performed together. In some embodiments, each of rotational and row alignment calibrations can be performed at different times, or frequencies. In some embodiments, rotational (column-oriented) calibration can be performed with less frequency on a given PCR or other machine than row-alignment calibration. In some embodiments, row-alignment calibration can be performed before each analytic run, or at other times.

According to various embodiments, the calibration analysis can comprise utilizing techniques to find peaks in all the signatures, for example, two signatures in the rotation calibration analysis, and one signature in the translation calibration image. The technique used to identify peaks can comprise a type of recursive processing techniques referred to herein as a "peak splitter" algorithm or module, a flowchart of which is illustrated, for example, in FIGS. 7A and 7B.

According to various embodiments, the peak splitter algorithm or module used to identify intensity peaks from individual wells 108 can consider averages of n-pixel wide segments of the intensity signature. The peak splitter algorithm or module can begin in step 702. In step 704, the first two adjacent segments (e.g., samples 1 to n and n+1 to 2n) can be accessed or retrieved, for instance, from a PCR or other machine, from a stored source, from a networked source, or from other data sources or stores. In step 706, the difference between the averages of the first and of the second n-pixel wide segments can be computed to determine the initial direction. In step 708, according to various embodiments, the peak splitter can perform an "extender" function or module that moves the two adjacent segments towards the end of the signature, by one sample. In step 710, once the adjacent segments are shifted or moved, the current direction can become the difference between the averages of the current first and of the current second adjacent segments. In step 712, a test can be administered to determine whether the current and initial directions are the same. If the directions are the same, processing can return to step 708. If the directions are different, processing can proceed to step 714.

According to various embodiments, when the updated and initial directions differ, the extender function or module can perform further tests. In step 714, a test can be administered to determine whether the number of samples spanned by the initial first segment and the current final segment is greater than or equal to an adjustable, dynamically calculated, or predetermined threshold number of samples. If the number of samples spanned is greater than the threshold number of samples, processing can proceed to step 718 where the extender function or module can declare a transition. According to various embodiments, when the extender function or module declares a transition, in step 720, the extender can save the sample indices of the initial segment and the current final segments, and in step 722, it can return the part of the signal that begins one sample past the first sample of the current final segment.

According to various embodiments, if the number of samples determined to be spanned by the initial first segment and the current final segment in step 714 is less than the adjustable, dynamically calculated, or predetermined threshold number of samples, the extender function or module can proceed to step 716 where it can set the initial direction computed from the current two adjacent segments, and return to step 706. The peak splitter algorithm or module can repeatedly call or execute the extender function or module until the extender has exhausted all the sample wells 108 or other calibration objects in the signature. In some embodiments, each pass through the extender processes only the part of the signal returned by the previous pass through the extender.

According to various embodiments, once the extender processing has finished, in step 724, the peak splitter algorithm or module can invoke or execute a "compute peaks" function or module, which can parse the list of transitions found by the extender. In step 726, if the adjacent transitions declared by the extender are increasing, then followed by a decreasing region, and the transitions or other features are separated by less than an adjustable, dynamically calculated, or predetermined threshold number of samples, the compute peaks function or module can declare candidate peaks. In step 728, for each candidate peak, the compute peaks function or module can create a mathematical model of the transition, for example, by computing a least squares quadratic fit. As an example, a least squares quadratic fit to samples in adjacent transitions can be computed. The maximum value of the model can be considered the peak intensity. In step 730, according to various embodiments, the peak position and intensity can be saved, for example, to electronic memory, local hard disk, or network storage, or other memory or storage device.

In step 732, according to various embodiments, the calibration analysis can comprise, after processing all the transitions, the compute peaks function or module which can make a determination whether the number of peaks found exceeds an adjustable, dynamically calculated, or predetermined peak number threshold. If in step 732 a determination has been made that too few peaks were discovered, for example, a number below a peak number threshold, for instance, the total number of wells 108, half of the total number of wells 108, or another number or threshold, then in step 734 the compute peaks function or module can declare an error, after which processing can end, repeat, return to a prior processing point, or proceed to a further processing point in step 738. If an error or anomaly is declared, detected or suspected, the calibration analysis can comprise corrections and/or compensations for the error.

According to various embodiments, if in step 732 a determination is made that too many peaks have been discovered above a number of an adjustable, dynamically calculated, or predetermined maximum peak threshold, then in step 736 the compute peaks function or module can execute a "determine best peaks" function or module. In step 736, the determine best peaks function or module can iteratively remove the smallest peaks, for example, until a desired, adjustable, dynamically calculated, or predetermined number of peaks remain, or until a statistical measure, for example, a z-score or standard deviation among remaining peaks, satisfy a desired, adjustable, dynamically calculated, or predetermined threshold or criterion. After the best peaks processing is complete, processing can end, repeat, return to a prior processing point, or proceed to a further processing point in step 738.

According to various embodiments, the positions of the wells 108 or other calibration objects in the rectangular grid or pattern or array in plate 106, can be tightly controlled during manufacture, allowing the calibration analysis to assume well separations and other measures are rigidly and accurately known, and therefore apply statistical tests to the rotational and translational positions that are computed. Results that fail these tests can indicate poor calibration procedures. If an error is detected or suspected, the calibration analysis can comprise correction and/or compensation for, and/or eliminate the error. In some embodiments, the calibration analysis can comprise a statistical z-score test, or other metric to validate features of the calibration analysis, for example, the separation of the columns in plate 106. Any column separation, for example, with a z-score less than an adjustable, dynamically calculated, or predetermined threshold, can indicate poor calibration procedures or results.

Figure 5:
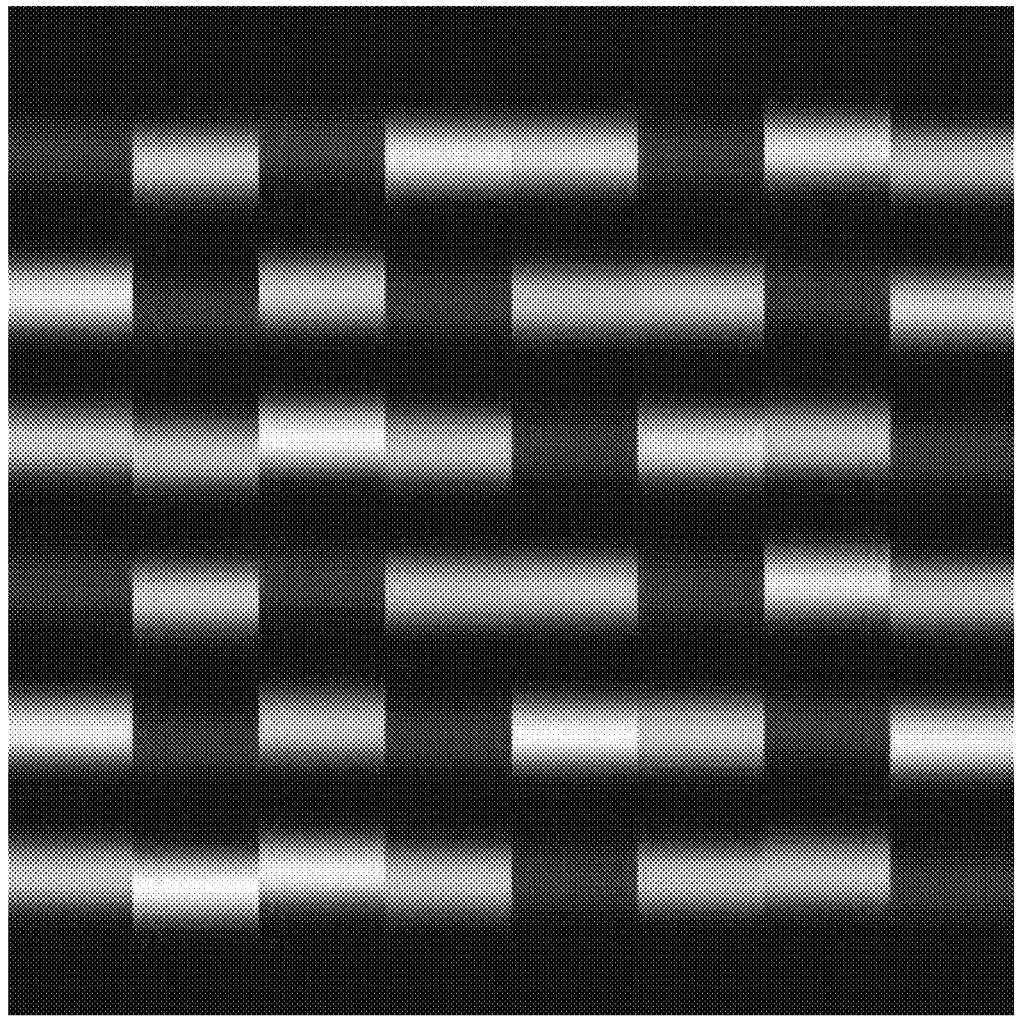
FIG. 5 illustrates a translation calibration image, according to various embodiments of the present teachings.

According to various embodiments, after finding and validating the column positions (rotational coordinates) of the wells 108 or other calibration objects, the calibration analysis can comprise, computing the column-dependant translational coordinates that will produce an undistorted or realigned image, for example, as illustrated in FIG. 5. To accomplish this, the calibration can comprise determining the row positions (translational coordinates) of the wells 108 or other calibration objects.

According to various embodiments, for each column position determined from the rotation calibration image (e.g., as illustrated in FIG. 2), that column of data obtained can be transmitted, as a signature, to the peak splitter algorithm or module. The peak splitter can compute the column coordinates (translational positions) of the peaks in the column signature. These positions can correspond to the positions in the column of the wells 108, or other calibration objects.

According to various embodiments, the calibration analysis can comprise computing, for each column position, the average translational separation of the wells 108 or other calibration objects, and subjecting these separations to a z-score or other test. In some embodiments, z-scores greater than an adjustable, dynamically calculated, or predetermined value can indicate poor calibration results.

According to various embodiments, the undistorted or realigned scan for each column can begin one separation before and one separation after the first and last well 108 in the column. Unique start and stop positions can be computed for each column. These start and stop positions can produce an undistorted or realigned image (e.g., as illustrated in FIG. 5) which has only as many image columns as there are columns of wells 108 or other calibration objects. According to various embodiments, the calibration analysis can comprise utilizing the processes described above to extract the translational positions of the wells 108 or other calibration objects.

According to various embodiments, as with the rotational and translational positions computed from the rotation calibration image (illustrated, e.g., in FIG. 2), the calibration can comprise applying a z-score test to the translational positions from the translation calibration image (e.g., as illustrated in FIG. 5). Z-scores greater than an adjustable, dynamically calculated, or predetermined threshold can indicate poor calibration results. In some embodiments, other statistical measures than z-scores can be used to threshold or analyze rotational, translational, or other position data.

According to various embodiments, different aspects of differential dissociation/melting curve analyses, and different aspects of the present teachings, can be applied to commercial systems and implementations, such as the Step One™ machine commercially available from Applied Biosystems, Foster City, Calif., and described, for example, in the publication entitled "Applied Biosystems Step One Real-Time PCR System Getting Started Guide," which is incorporated by reference in its entirety herein.

It will be appreciated that while various embodiments described above involve the calibration of one or more aspects of plate positioning and instrument reading, according to various embodiments more than one type of calibration can be performed, together or in sequence. While various aspects of the present teachings have been described with regard to calibration in one angular and one linear or translational direction or dimension, it will be appreciated that according to various embodiments, calibration can, for example, be performed in two linear dimensions. According to various embodiments, calibration can likewise be performed in three dimensions, for example including a vertical displacement. Calibration according to other geometric directions, dimensions, or properties can also be performed.

Various embodiments of the present teachings can be implemented, in whole or part, in digital electronic circuitry, optics, optronics, or in computer hardware, firmware, software, or in combinations thereof. Apparatus of the present teachings can be implemented in a computer program, software, code, or algorithm embodied in machine-readable media, such as electronic memory, CD-ROM or DVD discs, hard drives, or other storage device or media, for execution by a programmable processor. Various method steps according to the present teachings can be performed by a programmable processor executing a program of instructions to perform functions and processes according to the present teachings, by operating on input data and generating output. The present teachings can, for example, be implemented in one or more computer programs that are executable on a programmable system including at least one programmable processor coupled to receive data and instructions from, and to transmit data and instructions to, a data storage system or memory, at least one input device such as a keyboard and mouse, and at least one output device, such as, for example, a display or printer. Each computer program, algorithm, software, or code can be implemented in a high-level procedural or object-oriented programming language, or in assembly, machine, or other low-level language if desired. According to various embodiments, the code or language can be a compiled, interpreted, or otherwise processed for execution.

Various processes, methods, techniques, and algorithms can be executed on processors that can include, by way of example, both general and special purpose microprocessors, such as, for example, general-purpose microprocessors such as those manufactured by Intel Corp. or AMD Inc., digital signal processors, programmable controllers, or other processors or devices. In some embodiments, generally, a processor will receive instructions and data from a read-only memory and/or a random access memory. In some embodiments, a computer implementing one or more aspects of the present teachings can generally include one or more mass storage devices for storing data files, such as magnetic disks, internal hard disks, removable disks, magneto-optical disks, and CD-ROM DVD, Blu-Ray, or other optical disks or media. Memory or storage devices suitable for storing, encoding, or embodying computer program instructions or software and data can include, for instance, all forms of volatile and non-volatile memory, including for example semiconductor memory devices, such as random access memory, electronically programmable memory (EPROM), electronically erasable programmable memory, EEPROM, and flash memory devices, as well as magnetic disks internal hard disks, removable disks, magneto-optical disks, and optical disks. Any of the foregoing can be supplemented by, or incorporated in, ASICs. In some embodiments, processors, workstations, personal computers, storage arrays, servers, and other computer, information, or communication resources used to implement features of the present teachings can be networked or network-accessible.

Other embodiments will be apparent to those skilled in the art from consideration of the present specification and practice of the present teachings disclosed herein. For instance, while the various embodiments of the present teachings have been described as involving the positional calibration of sample plates in angular or polar terms, according to various embodiments, the present teachings can be applied to systems or techniques configured in [x,y] coordinates, or other coordinate systems. Similarly, while various embodiments have been described as related to aligning the planar orientation of a plate in a PCR machine, according to various embodiments, vertical alignment, or three-dimensional alignment, can be carried out according to the present teachings.

Likewise, while various embodiments have illustrated plate positioning and well detection in terms of a plate 106 having a regular, rectangular array of wells 108, according to various embodiments other patterns or groupings of wells 108, for example, circular, square, triangular, complex or irregular shapes or configurations of wells 108, can be used. Positional calibration, according to the present teachings, can, moreover, be carried out in detection systems other than PCR instruments. Resources described in various embodiments as singular can, in embodiments, be implemented as multiple or distributed, and resources described in various embodiments as distributed can be combined. It is intended that the present specification and examples be considered as exemplary only.

What is claimed is:

1. A computer-implemented method of calibrating an alignment of a sample support in a scanning instrument comprising a detector and processor, the method comprising:
   receiving, by the detector, emission data from a set of calibration objects of the sample support to generate a set of image data to form an image, wherein the sample support is configured to hold biological samples;
   identifying intensity peak data using the emission data in the image; determining, by the processor, a rotational position of a center of each calibration object in the set of the calibration objects in a first dimension of the image using the identified intensity peak data of the emission data, wherein determining the center comprises:
   determining a center corresponding to an angular position of an imaging element imaging the calibration objects,
   summing or differencing a set of peaks in the emission data for the set of calibration objects in the second dimension at the same angular value, and using the angular position and the summing or differencing the set of peaks in the emission data to determine the rotational position of the center of each calibration object;
   determining, by the processor, a set of translations of the set of calibration objects in a second dimension of the image using the emission data;
   generating, by the processor, a calibrated alignment of the set of calibration objects using the rotational position of the centers of each calibration object and the determined set of translations;
   generating a non-distorted representation of the sample support using the calibrated alignment of the set of calibration objects;
   calibrating the scanning instrument using the calibrated alignment; and
   scanning biological samples by the calibrated scanning instrument.

2. The computer-implemented method of claim 1, wherein determining a center comprises identifying a highest summation of emission data in the second dimension data in the second dimension, and associating the center with the angular value corresponding the highest summation of emission data.

3. The computer-implemented method of claim 1, wherein determining a set of translations comprises identifying a set of peaks in the emission data for a set of calibration objects in the second dimension.

4. The computer-implemented method of claim 1, further comprising generating a statistical measure of the separation distance between pairs of the set of calibration objects.

5. The computer-implemented method of claim 1, further comprising:
   determining a set of coordinates of the sample support for the detector to scan to collect emission data from the biological sample within the sample support based on the calibrated alignment of the set of calibration objects.

6. A system for analyzing biological samples, the system comprising:
   an input unit, the input unit being configured to receive emission data from a set of calibration objects of a sample support to generate a set of image data to form an image, wherein the sample support is configured to hold biological samples; and
   a processor unit, the processor unit communicating with the input unit and configured to: identify intensity peak data in the image using the emission data;
   determine a rotational position of a center of each calibration object in the set of the calibration objects in a first dimension of the image using the identified intensity peak data of the emission data, wherein determining the center comprises:
   determining a center corresponding to an angular position of an imaging element imaging the calibration objects,
   summing or differencing a set of peaks in the emission data for the set of calibration objects in the second dimension at the same angular value, and
   using the angular position and the summing or differencing the set of peaks in the emission data to determine the rotational position of the center of each calibration object;
   determine a set of translations of the set of calibration objects in a second dimension of the image using the emission data, generate a calibrated alignment of the calibration objects using the rotational position of the centers of each calibration object and the determined set of translations, generate a non-distorted representation of the sample support using the calibrated alignment of the set of calibration objects, calibrate the scanning instrument using the calibrated alignment, and control the calibrated scanning instrument to scan biological samples.

7. The system of claim 6, wherein determining a center comprises determining a center corresponding to an angular position of an imaging element imaging the calibration objects.

8. The system of claim 6, wherein determining a set of translations comprises identifying a set of peaks in the emission data for a set of calibration objects in the second dimension.

9. The system of claim 6, further comprising generating a statistical measure of the separation distance between pairs of the set of calibration objects.

10. The system of claim 6, further comprising:
a detector configured to scan a set of coordinates of the sample support to collect emission data from the biological sample within the sample support based on the calibrated alignment of the set of calibration objects.

11. A non-transitory computer-readable medium of a scanning instrument encoded with processor executable instructions, the instructions for:

receiving emission data from a set of calibration objects of the sample support to generate a set of image data to form an image, wherein the sample support is configured to hold biological samples;

identifying intensity peak data in the image using the emission data;

determining a rotational position of a center of each calibration objects in the set of the calibration objects in a first dimension of the image using the identified intensity peak data of the emission data, wherein determining the center comprises:

determining a center corresponding to an angular position of an imaging element imaging the calibration objects, summing or differencing a set of peaks in the emission data for the set of calibration objects in the second dimension at the same angular value, and using the angular position and the summing or differencing the set of peaks in the emission data to determine the rotational position of the center of each calibration object;

determining a set of translations of the set of calibration objects in a second dimension using the emission data;

generating a calibrated alignment of the set of calibration objects using the rotational position of each center of the calibration objects and the determined set of translations;

generating a non-distorted representation of the sample support using the calibrated alignment of the set of calibration objects;

calibrating the scanning instrument using the calibrating alignment; and controlling the calibrated scanning instrument to scan biological samples.

12. The non-transitory computer-readable medium of claim 11, wherein determining a center comprises determining a center corresponding to an angular position of an imaging element imaging the calibration objects.

13. The non-transitory computer-readable medium of claim 11, wherein the instructions are further for: generating a statistical measure of the separation distance between pairs of the set of calibration objects.

14. The non-transitory computer-readable medium of claim 11, wherein the sample support comprises a plate.

15. The non-transitory computer-readable medium of claim 11, wherein the instructions further comprise instructions for:

determining a set of coordinates of the sample support for the detector to scan to collect emission data from the biological sample within the sample support based on the calibrated alignment of the set of calibration objects.

* * * * *